United States Patent
Chen et al.

(10) Patent No.: US 9,144,590 B2
(45) Date of Patent: Sep. 29, 2015

(54) USE OF ASTER EXTRACT IN THE TREATMENT OF OPIOID-INDUCED CONSTIPATION

(75) Inventors: Jui-Ching Chen, New Taipei (TW);
Che-Yi Lin, New Taipei (TW);
Chien-Chang Wu, New Taipei (TW);
Cheng-Po Huang, New Taipei (TW);
Yuan-Ling Ku, New Taipei (TW);
Yueh-Chu Chen, New Taipei (TW);
Yu-Hsuan Lin, New Taipei (TW);
Chih-Sheng Hung, New Taipei (TW)

(73) Assignee: Medical and Pharmaceutical Industry Technology and Development Center, Taipei County (TW)

( * ) Notice: Subject to any disclaimer, the term of this patent is extended or adjusted under 35 U.S.C. 154(b) by 121 days.

(21) Appl. No.: 13/336,633

(22) Filed: Dec. 23, 2011

(65) Prior Publication Data
US 2012/0164251 A1 Jun. 28, 2012

(30) Foreign Application Priority Data
Dec. 23, 2010 (TW) .............................. 99145642 A

(51) Int. Cl.
*A61K 36/28* (2006.01)

(52) U.S. Cl.
CPC ............. *A61K 36/28* (2013.01); *A61K 2236/39* (2013.01)

(58) Field of Classification Search
None
See application file for complete search history.

(56) References Cited

FOREIGN PATENT DOCUMENTS

| CN | 1628713 A | * | 6/2005 |
| CN | 1872175 A | * | 12/2006 |

OTHER PUBLICATIONS

Caimian. "Discussion on Certain Issues of the Diagnosis". Web Publication Date: May 11, 2009. [Retrieved on: Apr. 30, 2013]. Retrieved from the Internet: <URL: http://tcmdiscovery.com/News/info/20090511__14062__3.html>.*
"American Family Physician: Management of Common Opiod-Induced Adverse Effects". Web Publication Date: Oct. 15, 2006 [Retrieved from the Internet on: Oct. 24, 2013]. Retrieved from:: <URL: http://www.aafp.org/afp/2006/1015/p1347.html>.*
"Medical News Today". Retrieved from the Internet on: Oct. 25, 2013. Retrieved from the Internet: <URL: http://www.medicalnewstoday.com/info/oic/treatment-for-opioid-induced-constipation>.*
Mr. Kent's Chemistry Page. "Like Dissolves Like and Molecule Ion Attractions". Retrieved from the Internet on: Jan. 26, 2015. Retrieved from: <URL: http://www.kentchemistry.com/links/bonding/LikeDissolveslike.htm>.*

* cited by examiner

*Primary Examiner* — Amy L Clark
(74) *Attorney, Agent, or Firm* — Muncy, Geissler, Olds & Lowe, P.C.

(57) ABSTRACT

Disclosed herein is the use of an extract from an Aster species for the preparation of a medicament for the treatment of opioid-induced constipation. The extract is extracted from fresh and/or dried roots and rhizomes of a Tatarian aster (*Aster tartaricus*) plant, in which the extraction uses water or 40-95% (v/v) ethanol as an extractant to obtain an extraction mixture. In some embodiments, the extraction mixture is then eluted with water followed by at least one eluent.

12 Claims, No Drawings

USE OF ASTER EXTRACT IN THE TREATMENT OF OPIOID-INDUCED CONSTIPATION

CROSS-REFERENCE TO RELATED APPLICATION

This application claims priority to Taiwan application no. 99145642, filed Dec. 23, 2010, the entireties of which is incorporated herein by reference.

BACKGROUND OF THE INVENTION

1. Field of the Invention

The present disclosure relates to the treatment of opioid-induced constipation (OIC). More particularly, the disclosure invention relates to the use of extract from Aster spp. in the treatment of opioid-induced constipation.

2. Description of Related Art

An opioid, in its widest sense, refers to a compound that binds to opioid receptors, which are distributed widely in the central and peripheral nervous system and the gastrointestinal tract. Opioids may be classified as natural, synthetic, or endogenous opioids. Natural opioids such as codeine and morphine are derived from opiate alkaloids contained in the opium poppy. Synthetic opioids refer to manmade compounds created by chemically modifying the natural opioids (e.g., oxycodone) or synthesized from non-opioid substances (e.g., methadone). Endogenous opioids are naturally produced by the body and include substances such as endorphins.

Opioids are commonly prescribed for their analgesic, or pain-killing, properties. However, opioid use carries several side effects, including drowsiness, nausea, vomiting, slower breathing, and a general depression of the respiratory system. Further, opioids often cause constipation, or more particularly, opioid-induced constipation. Accordingly, additional medicines are often required to be prescribed along with the opioid painkillers that cause the constipation. For example, laxatives and/or cathartics for use in the treatment of ordinary functional constipation are prescribed to treat opioid-induced constipation. A cathartic accelerates defecation, while a laxative eases defecation, usually by softening the stool; some medicines are considered to be both laxatives and cathartics. Although functional constipation and opioid-induced constipation share many signs and symptoms in common, treatments for functional constipation are not always successful in treating opioid-induced constipation. Therefore, targeted treatment for opioid-induced constipation has been pursued.

Oral opioid-receptor antagonists, including naloxone, naltrexone, and nalmefene have been suggested to be potentially helpful in ameliorating opioid effects in the gastrointestinal tract. However, these agents may be of limited use because they also cross the blood-brain barrier and can reverse analgesic effects of opioids, or induce uncomfortable opioid withdrawal symptoms. Methylnaltrexone is a newer agent that blocks peripheral opioid receptor. Therefore, methylnaltrexone may decrease the constipating effects of opioid pain medications in the gastrointestinal tract without affecting analgesia effects in the central nervous system. However, since up to 60 percent of opioid analgesia may be mediated by opioid receptors on peripheral sensory neurons, methylnaltrexone would increase pain under such circumstances.

In view of the foregoing, there exists in the art a need for a novel composition and method that treat opioid-induced constipation.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least in part, on the discovery that the extract form an *Aster tartaricus* (Tatarian aster) plant is effective in treating opioid-induced constipation. Therefore, one aspect of the present invention pertains to the use of an extract from Tatarian aster for the preparation of a medicament for the treatment of opioid-induced constipation.

According to embodiments of the present invention, the extract is prepared from a component of the plant of Tatarian aster. The plant component for use in the extraction may be a fresh or dried material collected from the rhizome and/or root of a Tatarian aster plant.

According to embodiments of the present invention, the preparation of the medicament comprises an extraction step, in which the component collected from the Tatarian aster is extracted with an extractant to produce an extraction mixture. Extractants suitable for use herein include water, and an alcoholic solution consisting of water and 10-95% (v/v) ethanol.

In one embodiment, the constitution of the solvent of the extraction mixture is altered to allow the formation of a precipitant, which is suitable for use in the preparation of the present medicament. For example, when the alcoholic solution is used as the extractant, water is added into the extraction mixture to give a precipitate. Alternatively, when water is used as the extractant, alcoholic solution is added into the extraction mixture to give a precipitate. Optionally, the precipitate may be dried to yield extract powders.

Alternatively, in some embodiments, the extraction mixture is subjected to a column chromatography in which the column is eluted with water followed by at least one eluents to obtain at least one eluate which is suitable for use in the preparation of the present medicament. Non-limiting examples of the eluent include, but are not limited to, 40-95% (v/v) ethanol, acetone, and 40-95% (v/v) ethanol with 0.1-1% (v/v) formic acid.

Optionally, extraction mixture is filtered, concentrated, and/or dried prior to being subjected to the column chromatography. Still optionally, the eluate is concentrated to reduce the volume of the eluate and remove the eluent from the concentrated eluate.

According to a first particular embodiment of the present invention, the preparation of the medicament comprises the steps as follows. A dried root or rhizome of a Tatarian aster plant, or a combination of both is extracted with water to produce an extraction mixture. Then the extraction mixture is subjected to a column chromatography by eluting the column with water followed by 95% (v/v) ethanol, and an eluate obtained from the column eluted with 95% (v/v) ethanol is collected.

According to a second particular embodiment of the present invention, the preparation of the medicament differs from the previous embodiment in that the column is eluted with water followed sequentially by (1) 40% (v/v) ethanol and (2) 95% (v/v) ethanol to obtain an eluate. Other than the elution step, the preparation processes of the first and second embodiments are substantially the same, in which an eluate obtained from the column eluted with 95% (v/v) ethanol is collected.

According to a third particular embodiment of the present invention, the preparation of the medicament comprises the steps as follows. A dried root or rhizome of a Tatarian aster plant, or a combination of both is extracted with 50% (v/v) ethanol to obtain an extraction mixture. Then the extraction mixture is subjected to a column chromatography by eluting the column with water followed by, sequentially, (1) 95% (v/v) ethanol, (2) acetone, (3) 95% (v/v) ethanol with 0.1% (v/v) formic acid, and (4) 50% (v/v) ethanol 0.1% (v/v) formic acid; and an eluate obtained from the column eluted with acetone, an eluate obtained from the column eluted with 95% (v/v) ethanol with 0.1% (v/v) formic acid, and an eluate obtained from the column eluted with 50% (v/v) ethanol 0.1% (v/v) formic acid are collected and combined.

According to a fourth particular embodiment of the present invention, the preparation of the medicament differs from the third embodiment provided hereinabove in that the column is eluted with water followed sequentially by (1) 70% (v/v) ethanol, (2) 95% (v/v) ethanol, (3) acetone, (4) 95% (v/v) ethanol with 0.1% (v/v) formic acid, and (5) 50% (v/v) ethanol 0.1% (v/v) formic acid to obtain an eluate to obtain an eluate. Other than the elution step, the preparation processes of the third and the fourth embodiments are substantially the same, in which an eluate obtained from the column eluted with 95% (v/v) ethanol, an eluate obtained from the column eluted with acetone, an eluate obtained from the column eluted with 95% (v/v) ethanol with 0.1% (v/v) formic acid, and an eluate obtained from the column eluted with 50% (v/v) ethanol 0.1% (v/v) formic acid are collected and combined.

According to a fifth particular embodiment of the present invention, the preparation of the medicament comprises the steps as follows. A dried root or rhizome of a Tatarian aster plant, or a combination of both is extracted with 95% (v/v) ethanol to obtain an extraction mixture. Then the extraction mixture is concentrated, and water is added therein to give a precipitate.

Another aspect of the present invention pertains to a method of treating opioid-induced constipation in a subject in need thereof. In practice, the method comprises administering to the subject an effective amount of an extract from Tatarian aster. Specifically, the extract from Tatarian aster for use in the present method is prepared in accordance with the preparation process provided in various embodiments of the present invention.

Many of the attendant features and advantages of the present disclosure will become better understood with reference to the following detailed description.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "treatment" includes preventative (e.g., prophylactic), curative or palliative treatment, and the term "treating" also includes preventative (e.g., prophylactic), curative or palliative treatment. In particular, the term "treating" herein refers to the application or administration of the medicament of the present invention to a subject, who has a medical condition, a symptom of the condition, or a predisposition toward the condition, with the purpose to partially or completely alleviate, ameliorate, relieve, delay onset of, inhibit progression of, reduce severity of, and/or reduce incidence of one or more symptoms or features of a particular condition. Treatment may be administered to a subject who does not exhibit signs of a condition and/or to a subject who exhibits only early signs of a condition for the purpose of decreasing the risk of developing pathology associated with the condition.

The term "effective amount" as used herein refers to the quantity of a medicament which is sufficient to yield a desired therapeutic response. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, as the total mass of the medicament (e.g., in grams, milligrams or micrograms) or a ratio of mass of the medicament to body mass, e.g., as milligrams per kilogram (mg/kg).

As used herein, the term "constipation" refers to a physical condition that includes at least one of the following conditions, reduced frequency of bowel movements, hardening of feces, and difficulty in passing feces. The term "functional constipation" refers generally to constipation that is not due to any underlying physical or physiological cause such as medication side effects or an underlying medical condition. The term "opioid-induced constipation" refers to constipation resulting from opioid drugs.

The term "opioid" generally refers to a compound that binds to opioid receptors. As used herein, the term "opioid drug" encompasses all natural and synthetic opioids. In particular, opioid drugs are not limited to compounds with morphine-like, painkilling (analgesic) effect; rather, they includes drugs acting on opioid receptors present in the central nervous system and/or peripheral system, as well as those acting on opioid receptors present in the gastrointestinal tract. Illustrative examples of natural opioid include, but are not limited to, morphine, codeine, thebaine, and salvinorin A. Synthetic opioids include semi-synthetic opium alkaloids derivatives such as heroin (diacetylmorphine), dihydrocodeine, hydromorphone, nicomorphine, and oxycodone. Illustrative examples of fully synthetic opioid drugs include, but are not limited to, anilidopiperidines (e.g., fentanyl), phenylpiperidines (e.g., pethidine), diphenylpropylamine derivatives (e.g., loperamide), benzomorphan derivatives (e.g., dezocine), oripavine derivatives (e.g., buprenorphine), and morphinan derivatives (e.g., butorphanol).

As used herein, the term "fresh" refers to plant components that have not (yet) been processed, or only minimally processed (e.g., cut or sliced and/or packaged) after harvest and which are not preserved by substantive drying. Furthermore, the term "fresh" does not necessarily require a strict time-dependency. Rather, it is used solely to differentiate between dried plant components and non-dried plant components.

As used herein the term "dried" refers to a range of moisture contents typically observed when a plant component is dehydrated. The drying can occur by any means known in the art, including sun drying, oven drying and freeze drying. Moisture contents in dried plant components can range from 1 to 20% by weight, however, typical ranges are between 2 and 5%.

The terms "extract from a Tatarian aster plant" or "plant extract," as used herein, refer to a composition prepared by contacting plant components from the Tatarian aster plant with a solvent following standard procedures such as those described herein. The term encompasses crude extracts as well as processed or refined extract. Specifically, crude extracts are prepared by a simple extraction, whereas processed or refined extracts are obtained by subjecting the crude extracts to one or more separation and/or purification steps. The plant extract may be in liquid form, such as a solution, concentrate, or distillate; or it may be in solid form in which the solvent is removed, such as in granulate or powder form.

Generally, plant extracts are prepared by contacting selected plant components with at least one extractant. In some optional cases, the thus-obtained extraction mixtures are later subjected to one or more separation and/or purification steps. However, the present inventor unexpectedly discover that some, but not all, extracts form Tatarian aster is effective in treating opioid-induced constipation. Therefore, one aspect of the present invention pertains to the use of an extract from Tatarian aster for the preparation of a medicament for the treatment of opioid-induced constipation.

In particular, extracts form Tatarian aster suitable for use in treating opioid-induced constipation are prepared in accordance with processes set forth hereinbelow. First, in an extraction step, plant components collected from Tatarian aster plants are extracted with an extractant to obtain an extraction mixture. Then, in a separation step, the extraction mixture is subjected to column chromatography or precipitation.

According to embodiments of the present invention, the plant component suitable for use in the extraction is a fresh or dried material collected from the rhizome and/or root of a Tatarian aster plant.

In some embodiments, the extractant is water; whereas in some other embodiments, the extractant is an alcoholic solution consisting of water and 10-95% (v/v) ethanol. For example, the alcohol solution may be any of 10, 15, 20, 25, 30, 35, 40, 45, 50, 55, 60, 65, 70, 75, 80, 85, 90, and 95% (v/v) ethanol.

In optional embodiments, the extraction mixture is filtered, concentrated, and/or dried before the separation step.

In one embodiment, the extraction mixture is subjected to a reduced-pressure concentration to obtain a concentrate, and then the concentrate is washed with water to obtain a precipitate, which is suitable for use in the preparation of the present medicament. Optionally, the precipitate may be dried to yield extract powders, which is also suitable for use in the preparation of the present medicament.

In some alternative embodiments, the extraction mixture is subjected to a column chromatography in which the column is eluted with water followed by at least one eluents to obtain at least one eluate. Optionally, the eluate is concentrated to reduce the volume of the eluate and remove the eluent from the concentrated eluate. Still optionally, the concentrated eluate is dried to yield extract powders. According to principles and spirits of the present invention, the eluate, concentrated eluate, and extract powders are respectively suitable for use in the preparation of the present medicament.

Non-limiting examples of the eluent for use in the column chromatography include, but are not limited to, 40-95% (v/v) ethanol, acetone, and 40-95% (v/v) ethanol with 0.1-1% (v/v) formic acid.

Another aspect of the present invention pertains to a method of treating opioid-induced constipation in a subject in need thereof. Particularly, the present invention is related to a method of treating OIC that responds poorly to current commercially available constipation drugs, which include, but are not limited to, lactulose, magnesium oxide, and sennoside A&B. In practice, the method comprises administering to the subject an effective amount of an extract from an extract from Tatarian aster. Specifically, the extract from Tatarian aster for use in the present method is prepared in accordance with the preparation process provided in various embodiments of the present invention.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example 1

Preparation of Extracts from Tatarian Aster 1.1 Water Extraction

Dried, sliced components (roots and rhizomes) of Tatarian aster (purchased from Jin Han Hon Co., Ltd., Kaohsiung, Taiwan) were boiled and refluxed in reverse osmotic (RO) water in a ratio of 1:10 of plant component to water (w/w) for about 1 hour to obtain a crude extract. The crude extract was sifted through a 350-mesh sieve, and then filtered through a filter membrane having a pore size of 5 μm to give an aqueous water-extraction mixture. The water-extraction mixture was concentrated dried by freeze-drying to yield water-extracted powders.

1.1.1 Column Chromatography A

The water-extracted powders from example 1.1 were reconstituted in RO water and loaded onto a Diaion HP20 column (Diaion, Mitsubishi Chemistry Inc.) in which the weight ratio of the water-extracted powders to the dry column is about 1:30. Thereafter, the column was sequentially eluted by 3 bed volumes of RO water and 3 bed volumes of 95%

(v/v) ethanol, and the eluate obtained from the column eluted with 95% (v/v) ethanol was collected. The eluate was concentrated to a suitable volume, and the ethanol is substantially removed from the concentrated eluate, which was later freeze-dried to yield eluted powders (hereinafter, Powder A).

1.1.2 Column Chromatography B

The water-extracted powders from example 1.1 were reconstituted in RO water and loaded onto a Diaion HP20 column (Diaion, Mitsubishi Chemistry Inc.) in which the weight ratio of the water-extracted powders to the dry column is about 1:20. Thereafter, the column was sequentially eluted by 3 bed volumes of RO water, 3 bed volumes of 40% (v/v), and 3 bed volumes of 95% (v/v) ethanol, and the eluate obtained from the column eluted with 95% (v/v) ethanol was collected. The eluate was concentrated to a suitable volume, and the ethanol is substantially removed from the concentrated eluate, which was later freeze-dried to yield eluted powders (hereinafter, Powder B).

1.2 50% (v/v) Ethanol Extraction

The extraction process of this example was similar to the water extraction described in above example 1.1 except that 50% (v/v) ethanol was used as the extractant to obtain a 50% ethanol-extraction mixture. The 50% ethanol-extraction mixture was concentrated by evaporation, and then dried to yield 50% ethanol-extracted powders by freeze-drying.

1.2.1 Column Chromatography C

The 50% ethanol-extracted powders from example 1.2 were reconstituted in 50% ethanol and loaded onto a Diaion HP20 column (Diaion, Mitsubishi Chemistry Inc.) in which the weight ratio of the 50% ethanol-extracted powders to the dry column is about 1:20. Thereafter, the column was sequentially eluted by 3 bed volumes of RO water, 3 bed volume of 95% (v/v) ethanol, 2 bed volumes of acetone, 2 bed volumes of 95% (v/v) ethanol with 0.1% (v/v) formic acid, and 1 bed volume of 50% (v/v) ethanol with 0.1% (v/v) formic acid to obtain respective eluates. The eluates obtained from the columns eluted with acetone, 95% (v/v) ethanol with 0.1% (v/v) formic acid, and 50% (v/v) ethanol with 0.1% (v/v) formic acid were collected and combined. The combined eluate was then concentrated to a suitable volume, and the ethanol and acetone are substantially removed from the concentrated eluate, which was later freeze-dried to yield eluted powders (hereinafter, Powder C).

1.2.2 Column Chromatography D

The 50% ethanol-extraction mixture from example 1.2 were loaded onto a Diaion HP20 column (Diaion, Mitsubishi Chemistry Inc.) in which the weight ratio of the 50% ethanol-extracted powders to the dry column is about 1:20. Thereafter, the column was sequentially eluted by 3 bed volumes of RO water, 3 columns volume of 70% (v/v) ethanol, 3 bed volume of 95% (v/v) ethanol, 2 bed volumes of acetone, 2 bed volumes of 95% (v/v) ethanol with 0.1% (v/v) formic acid, and 1 bed volume of 50% (v/v) ethanol with 0.1% (v/v) formic acid to obtain respective eluates. The eluates obtained from the columns eluted with 95% (v/v) ethanol, acetone, 95% (v/v) ethanol with 0.1% (v/v) formic acid, and 50% (v/v) ethanol with 0.1% (v/v) formic acid were collected and combined. The combined eluate was then concentrated to a suitable volume, and the ethanol and acetone are substantially removed from the concentrated eluate, which was later freeze-dried to yield eluted powders (hereinafter, Powder D).

1.3 95% (v/v) Ethanol Extraction and Precipitation

Dried, sliced components (roots and rhizomes) of Tatarian aster were boiled and refluxed in 95% (v/v) ethanol in a ratio of 1:10 of plant component to water (w/w) for about 1 hour to obtain a crude extract. The crude extract was sifted through a 350-mesh sieve, and the aqueous filtrate was collected and then suction filtered through a No. 2 filter paper (purchased from Toyo Roshi Kaisha Ltd., Japan) to obtain an aqueous extraction mixture. The extraction mixture was concentrated by reduced-pressure concentration to half of the original volume, and then RO water was added in a ratio of 1:1 (w/w) to allow the formation of precipitates. The precipitates were centrifuged, and the sediments were collected and freeze-dried to yield precipitate powders (hereinafter, Powder E).

Example 2

Measurement of Intestinal Transit Time 2.1 Materials

Tatarian aster extracts were prepared in accordance with the method set forth in above Example 1. Various anti-constipation drugs were obtained from commercial sources; these drugs including, LACTUL® Syrup (containing 666 mg/mL lactulose, purchased from Sinphar Pharm. Co., Ltd., Taiwan), Magnesium Oxide Tablet (containing 250 mg/tab MgO, purchased from Synpac-Kingdom Pharm. Co., Ltd., Taiwan), Sennapur® tablet (containing 12.5/tab sennoside A&B, purchased from Sawai Pharm. Co., Ltd., Japan). Loperamide HCl (purchased from Sigma, USA) was used to reduce intestinal transit. Other compounds used in the test included carboxymethylcellulose (CMC, purchased from Sigma, USA), and Tween 80 (purchased from Sigma, USA).

For administration, powders A and B were dispersed in water, respectively; powders C to E were dispersed in CMC respectively; and MgO tablet and Sennapur® tablet were grounded and then dispersed in Tween 80, respectively. The compositions were administered at 10 mL/kg/dose, and the concentration of the active ingredient in each composition was adjusted according to the specified dosage in each test.

2.2 Animal Models for Intestinal Transit

The experimental procedures were approved by the Institutional Animal Care and Use Committee (IACUC) of Ricerca Biosciences, LLC (Taiwan) and conducted according to national animal welfare regulations.

Male ICR mice were purchased from BioLASCO Taiwan Co., Ltd. (Taiwan) and kept in an air-conditioned animal shelter at room temperature of 22° C. to 24° C. with controlled level of humidity (40% to 50%) in a 12-hour light-dark cycle. Each mouse weighed between 30 g to 36 g at the beginning of the test. Tap water and standard laboratory rodent chow were provided ad libitum.

Each group comprised 10 mice. Extracts and anti-constipation drugs, unless otherwise specified, were administered orally to separate experimental groups of mice at dosages specified in Table 1 below. Each mice received two dosages at day 1, and received one dosage at day 2 about 1 hour prior to the subcutaneous injection of loperamide HCL (0.7 mg/kg). Sennoside A&B was orally administered once at day 1 around 5:30 pm, and another dosage was given one hour prior to the subcutaneous injection of loperamide HCL.

Animals of each vehicle group were given the vehicle used in the corresponding experimental group via the same administration route and dosage as specified. Loperamide HCl (0.7 mg/kg) was subcutaneously injected one hour after the administration of the last dose of the vehicle. For the sham groups, the animals were neither treated with any plant extracts or anti-constipation drugs nor injected with loperamide HCl.

Generally, atropine or morphine was used to establish animal model for intestinal transit, whereas loperamide was used to establish animal model for gastric emptying. However, due to the likelihood that atropine or morphine might result in addiction, loperamide was used in the present invention. Since loperamide, like morphine, decreases the tone of the longitudinal smooth muscles but increases the tone of circular smooth muscles of the intestinal wall, it would increases the amount of time substances stay in the intestine. Also, loperamide is known to decrease colonic mass movements and suppress the gastrocolic reflex. Therefore, loperamide is a suitable substitute for morphine in establishing animal model for intestinal transit to investigate opioid-induced constipation.

About 30 minutes after the loperamide injection, a glass bead having diameter of about 3 mm was stuffed into the distal colon, which is about 2 cm from the anal aperture of each mouse, and the mouse was monitored so as to record the time took for the mouse to discharge the glass bead.

All results are expressed as means±SE; n refers to animals in each group. Differences between animals of each group were compared by one-way ANOVA followed by Dunnett's t test. A p value less than or equal to 0.05 was considered to be statistically significant. Statistical analysis indicated that the groups treated with Tatarian aster extracts were significantly different ($p<0.05$) from vehicle group. Results were summarized in Table 1 below.

2.3 Results

In studying the effects of the Tatarian aster extracs on intestinal transit, the comparison of the glass bead discharge times between mice receiving the extract treatments and vehicle treatments, was used as the main criterion of assessment. Table 1 below shows the effects of these treatments by using the discharge times as an index.

TABLE 1

| Drug | Dosage (mg/kg per dosage) | Discharge Time for Tested Drugs (min) | Discharge Time for Sham (min) | Discharge Time for Vehicle/Loperamide (min) | Drug/Vehicle Relative Discharge Time (%) |
|---|---|---|---|---|---|
| Powder A | 100 | 22 ± 3 | 13 ± 2 | $H_2O$: 43 ± 7 | 51 |
| Powder B | 10 | 14 ± 2 | 14 ± 2 | $H_2O$: 44 ± 6 | 32 |
| Powder C | 10 | 20 ± 4 | 15 ± 2 | 2% CMC: 43 ± 5 | 47 |
|  | 30 | 25 ± 5 |  |  | 58 |
|  | 100 | 28 ± 4 |  |  | 65 |
|  | 500 | 29 ± 5 |  |  | 67 |
|  | 1000 | 27 ± 4 |  |  | 63 |
| Powder D | 10 | 22 ± 3 | 8 ± 1 | 2% CMC: 53 ± 7 | 42 |
| Powder E | 10 | 31 ± 4 | 6 ± 1 | 2% CMC: 49 ± 5 | 63 |
| LACTUL ® | 5 mL/kg | 46 ± 3 | 14 ± 1 | $H_2O$: 45 ± 4 | 102 |
| MgO | 250 | 49 ± 5 | 6 ± 1 | 2% Tween80: 49 ± 5 | 100 |
| Sennapur ® | 10 | 40 ± 5 | 6 ± 1 | 2% Tween80: 49 ± 5 | 82 |

As compared with the sham groups, the discharge times of vehicle groups were significantly prolonged, suggesting that loperamide was effective in establishing animal model for intestinal transit to investigate opioid-induced constipation. It was also observed that commercially available anti-constipation drugs were not effective in ameliorating constipation induced by loperanide.

By contrast, most Tatarian aster extracts (Powders A to E) treatment at specified dosage significantly reduced the discharge time compared to the vehicles. It's noticeable that Powder B administered at 10 mg/kg per dosage was the most effective one among the five extracts at tested dosages (relative discharge time: 32%).

These results indicate that Tatarian aster extracts prepared by the extractants and eluents described hereinabove are useful for treating opioid-induced constipation. However, other Tatarian aster extracts prepared by other extractants and eluents (data not shown) were not as effective as the present Tatarian aster extracts (Powders A to E).

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating opioid-induced constipation in a subject in need thereof consisting essentially of, administering to the subject a composition consisting of an effective amount of a water or aqueous ethanol extract of dried Tatarian aster roots and/or rhizomes for treating opioid-induced constipation in the subject.

2. The method of claim 1, wherein the water extract of dried Tatarian aster roots and/or rhizomes is prepared by a method comprising:
   extracting dried Tatarian aster roots and/or rhizomes with water to produce an extraction mixture; and
   subjecting the extraction mixture to column chromatography, wherein a column is eluted with water followed by an eluent of 95% (v/v) ethanol, and collecting an eluate obtained from the column eluted by the 95% (v/v) ethanol.

3. The method of claim 1, wherein the water extract of dried Tatarian aster roots and/or rhizomes is prepared by a method comprising:
   extracting dried Tatarian aster roots and/or rhizomes with water to produce an extraction mixture; and
   subjecting the extraction mixture to column chromatography, wherein a column is eluted with water, 40% (v/v) ethanol, and 95% (v/v) ethanol, and collecting an eluate obtained from the column eluted by the 95% (v/v) ethanol.

4. The method of claim 1, wherein the aqueous ethanol extract of dried Tatarian aster roots and/or rhizomes is prepared by a method comprising:

extracting dried Tatarian aster roots and/or rhizomes with 50% (v/v) ethanol to produce an extraction mixture; and subjecting the extraction mixture to column chromatography, wherein a column is eluted with water, 95% (v/v) ethanol, acetone, 95% (v/v) ethanol with 0.1% (v/v) formic acid, and 50% (v/v) ethanol with 0.1% (v/v) formic acid, and collecting and combining an eluate obtained from the column eluted by the acetone, an eluate obtained from the column eluted by the 95% (v/v) ethanol with 0.1% (v/v) formic acid, and an eluate obtained from the column eluted by the 50% (v/v) ethanol with 0.1% (v/v) formic acid.

5. The method of claim 1, wherein the aqueous ethanol extract of dried Tatarian aster roots and/or rhizomes is prepared by a method comprising:

extracting dried Tatarian aster roots and/or rhizomes with 50% (v/v) ethanol to produce an extraction mixture;

subjecting the extraction mixture to column chromatography, wherein a column is eluted with water, 70% (v/v) ethanol, 95% (v/v) ethanol, acetone, 95% (v/v) ethanol with 0.1% (v/v) formic acid, and 50% (v/v) ethanol with 0.1% (v/v) formic acid, and collecting and combining an eluate obtained from the column eluted by the 95% (v/v) ethanol, an eluate obtained from the column eluted by the acetone, an eluate obtained from the column eluted by the 95% (v/v) ethanol with 0.1% (v/v) formic acid, and an eluate obtained from the column eluted by the 50% (Or) ethanol with 0.1% (v/v) formic acid.

6. The method of claim 1, wherein the aqueous ethanol extract of dried Tatarian aster roots and/or rhizomes is prepared by a method comprising:

extracting dried Tatarian aster roots and or rhizomes with 95% (v/v) ethanol to obtain an extraction mixture; and adding water to the extraction mixture to give a precipitate.

7. The method of claim 1, wherein the water or aqueous ethanol extract of dried Tatarian aster roots and/or rhizomes is prepared by a method comprising: extracting dried Tatarian aster roots and/or rhizomes with water or aqueous ethanol to obtain an extraction mixture.

8. The method of claim 7, wherein the water extract of dried Tatarian aster roots and/or rhizomes is prepared by a method comprising: extracting dried Tatarian aster roots and/or rhizomes with water to obtain the extraction mixture.

9. The method of claim 7, wherein the aqueous ethanol extract of dried Tatarian aster roots and/or rhizomes is prepared by a method comprising: extracting the dried Tatarian aster roots and/or rhizomes with 10-95% (v/v) aqueous ethanol to obtain the extraction mixture.

10. The method of claim 7, wherein the extraction mixture is subjected to column chromatography, by eluting a column with water followed by at least one eluent to obtain at least one eluate, wherein the at least one eluent is selected from the group consisting of 40-95% (v/v) ethanol, 40-95% (v/v) ethanol with 0.1-1% (v/v) formic acid, and acetone.

11. The method of claim 10, wherein the extraction mixture is processed by at least one of: filtration, concentration, and drying before being subjected to column chromatography.

12. The method of claim 10, wherein the preparation method further comprises concentrating the eluate to provide a reduced volume of eluate by removing the eluent.

* * * * *